United States Patent
Kamins et al.

(10) Patent No.: US 7,880,318 B1
(45) Date of Patent: Feb. 1, 2011

(54) SENSING SYSTEM AND METHOD OF MAKING THE SAME

(75) Inventors: Theodore I. Kamins, Palo Alto, CA (US); Zhiyong Li, Palo Alto, CA (US); Duncan R. Stewart, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 466 days.

(21) Appl. No.: 11/741,242

(22) Filed: Apr. 27, 2007

(51) Int. Cl.
*H01L 23/58* (2006.01)
*H01L 29/221* (2006.01)
*H01L 33/00* (2010.01)
*H01L 21/00* (2006.01)
*G01B 5/28* (2006.01)

(52) U.S. Cl. ............ 257/798; 257/96; 257/E21.404; 257/E29.07; 257/E29.071; 257/E29.245; 438/800; 977/762; 977/773; 977/774; 977/775; 977/776; 977/777; 73/105

(58) Field of Classification Search ............ 257/96, 257/798, E21.404, E29.07, E29.071, E29.245; 73/105; 438/800; 977/762, 773–777
See application file for complete search history.

(56) References Cited

U.S. PATENT DOCUMENTS

| | | | |
|---|---|---|---|
| 6,518,156 B1 | 2/2003 | Chen et al. | |
| 6,894,359 B2 | 5/2005 | Bradley et al. | |
| 7,064,372 B2 * | 6/2006 | Duan et al. | 257/296 |
| 7,087,920 B1 * | 8/2006 | Kamins | 257/2 |
| 7,357,018 B2 * | 4/2008 | Curry et al. | 73/105 |
| 7,569,941 B2 * | 8/2009 | Majumdar et al. | 257/798 |
| 7,608,854 B2 * | 10/2009 | Kamins | 257/24 |
| 7,662,659 B2 * | 2/2010 | Kobayashi et al. | 438/99 |
| 7,745,813 B2 * | 6/2010 | Samuelson et al. | 257/12 |
| 2005/0133476 A1 | 6/2005 | Islam et al. | |
| 2006/0097389 A1 | 5/2006 | Islam et al. | |
| 2006/0159916 A1 | 7/2006 | Dubrow et al. | |
| 2006/0237805 A1 | 10/2006 | Segal et al. | |
| 2007/0048181 A1 | 3/2007 | Chang et al. | |
| 2007/0048492 A1 | 3/2007 | Lieber et al. | |
| 2007/0186629 A1 * | 8/2007 | Chang et al. | 73/105 |
| 2010/0096618 A1 * | 4/2010 | Iacopi et al. | 257/14 |

* cited by examiner

*Primary Examiner*—Ida M Soward

(57) ABSTRACT

A sensing system includes a nanowire, a passivation layer established on at least a portion of the nanowire, and a barrier layer established on the passivation layer.

15 Claims, 1 Drawing Sheet

SENSING SYSTEM AND METHOD OF MAKING THE SAME

BACKGROUND

The present disclosure relates generally to sensing systems and methods of making the same.

Since the inception of semiconductor technology, a consistent trend has been toward the development of smaller device dimensions and higher device densities. As a result, nanotechnology has seen explosive growth and generated considerable interest. Nanotechnology is centered on the fabrication and application of nano-scale structures, or structures having dimensions that are often 5 to 100 times smaller than conventional semiconductor structures. Nanowires are included in the category of nano-scale structures.

Nanowires are wire-like structures having at least one linear dimension (e.g., diameter) ranging from about 0.5 nm to about 200 nm. Nanowires are suitable for use in a variety of applications, including functioning as conventional wires for interconnection applications or as semiconductor devices. Nanowires are also the building blocks of many potential nano-scale devices, such as nano-scale field effect transistors (FETs), p-n diodes, light emitting diodes (LEDs) and nanowire-based sensors, to name a few. Nanowires have intrinsically large surface-to-volume ratios; as such, their physical properties (including electrical, mechanical and optical properties) are generally very sensitive to changes at the nanowire surfaces. This makes nanowires well suited for use as sensor devices. However, nanowire-based sensors may, in many instances, experience drawbacks, e.g., uncontrolled sensor drift, temporal fluctuations (e.g., noise), variations between devices, and chemical and/or electrical degradation and destabilization over time.

BRIEF DESCRIPTION OF THE DRAWINGS

Features and advantages of embodiments of the present disclosure will become apparent by reference to the following detailed description and drawings, in which like reference numerals correspond to similar, though not necessarily identical, components. For the sake of brevity, reference numerals or features having a previously described function may not necessarily be described in connection with other drawings in which they appear.

DETAILED DESCRIPTION

Embodiments of the sensing system disclosed herein advantageously include layer(s) that substantially reduce the chemical degradation of the nanowire. It is believed that these layer(s) substantially increase the stability of the nanowire and substantially decrease the opportunity for the sensor response to drift. Without being bound to any theory, it is believed that the layer(s) may, in some instances, also reduce surface/interface states that are capable of storing electronic charge and deleteriously affecting the electrical properties of the nanowire. Some embodiments of the sensing system may also include a functionalized nanoparticle located at a tip or end of the nanowire. This embodiment may advantageously be used to limit the sensing site(s) to a predetermined location.

Figure 1:
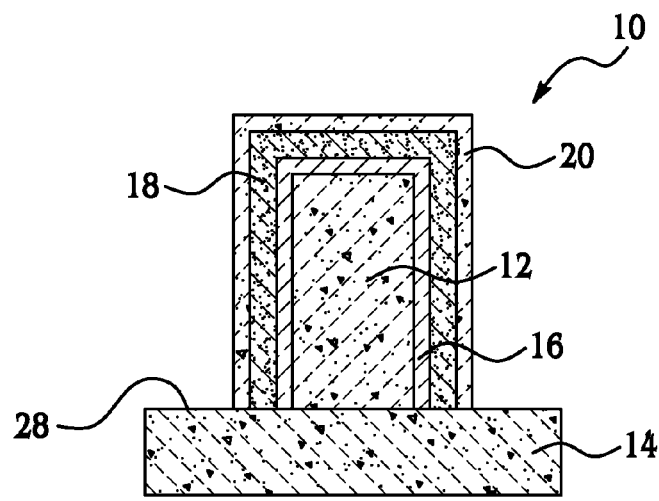
FIG. 1 is a schematic cross-sectional diagram of an embodiment of a sensing system.
Figure 2:
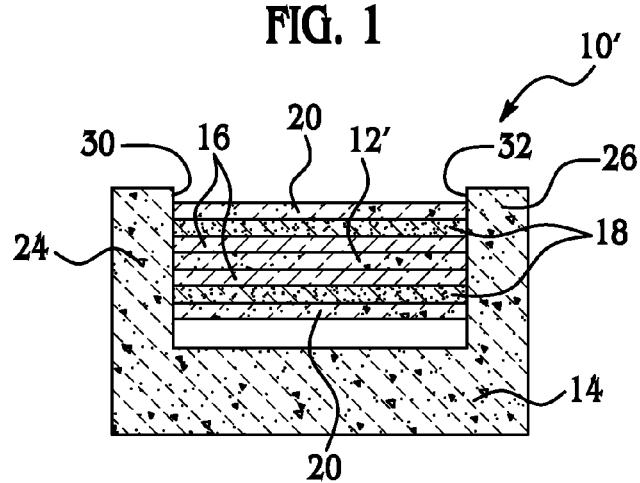
FIG. 2 is a schematic cross-sectional diagram of another embodiment of the sensing system.

Referring now to FIGS. 1 and 2, embodiments of the sensing device 10, 10' are depicted. Generally, embodiments of the sensing device 10, 10' include a nanowire 12, 12' attached to a substrate 14. The embodiment of FIG. 1 illustrates a substantially vertical nanowire 12 attached to the substrate 14, and the embodiment of FIG. 2 illustrates a substantially horizontal nanowire 12' attached to posts 24, 26 that are established on, or are formed from the substrate 14. While these embodiments are shown to include a single nanowire 12, 12', it is to be understood that a plurality of nanowires 12, 12' may be attached to the substrate 14.

As used herein, the term "attached to" is broadly defined to encompass a variety of divergent arrangements and assembly techniques. These arrangements and techniques include, but are not limited to (1) the direct attachment of one material to another material with no intervening materials therebetween; and (2) the attachment of one material to another material via one or more additional materials, provided that the one material being "attached to" the other material is somehow "supported" by the other material (notwithstanding the presence of one or more additional materials). For example, in FIG. 1, functional coating 20 is directly attached to barrier layer 18, but is also attached to nanowire 12 via layers 16 and 18.

Referring now to FIG. 1, the embodiment of the sensing device 10 includes a nanowire 12 established substantially vertically on a surface 28 of the substrate 14. Non-limiting examples of suitable substrates 14 include Si, Ge, silicon-on-insulator on a Si wafer (SOI), germanium on insulator on a Si wafer (GOI), silicon-on-sapphire (SOS), silicon-on-ceramic (SOC), and/or the like, and/or combinations thereof.

In one embodiment, the nanowire 12 is grown from the substrate surface 28. Often, the surface plane from which the nanowire 12 is grown has a (111) crystal lattice plane. In this embodiment, the (111) plane is considered to be horizontally oriented with respect to the Cartesian coordinate system. In this embodiment, the term "horizontal" generally refers to a direction or a plane that is substantially parallel with the surface 28, while the term "vertical" generally refers to a direction or plane that is substantially or approximately perpendicular to the surface 28. It is to be understood that the specific use of the terms "horizontal" and "vertical" throughout this disclosure to describe relative characteristics is to facilitate discussion, and is not intended to limit embodiments of the present disclosure.

Any suitable method may be used to grow the nanowire(s) 12. In some embodiments, the (111) surface orientation enables growth of the nanowire(s) 12 perpendicular to the surface (i.e., in this embodiment, in a vertical direction). In an embodiment, nanowire 12 growth is accomplished by establishing a catalyst nanoparticle (shown as 22 in FIG. 3) on surface 28, and exposing the catalyst nanoparticle to a precursor gas that initiates growth of the nanowire 12. As shown in FIG. 1, the catalyst nanoparticle may be removed once growth is accomplished. The formation of nanowires 12 is further described in U.S. patent application Ser. No. 10/982,051, filed on Nov. 5, 2004 (U.S. Publication No. 2006/0097389, published May 11, 2006), incorporated by reference herein in its entirety.

Non-limiting examples of the types of nanowires 12 that may be formed include silicon nanowires, germanium nanowires, silicon-germanium nanowires, compound semiconductor nanowires (including lattice mis-matched nanowires (e.g., indium phosphide nanowires (non-limiting examples of III-V nanowires) grown on silicon with a lattice mis-match of about 8%)), other III-V nanowires, II-VI nanowires, or the like, or combinations thereof.

Referring now to FIG. 2, the embodiment of the sensing device 10' includes a nanowire 12' established substantially horizontally between two posts 24, 26. In one embodiment, the posts 24, 26 are pre-formed and are attached to the substrate surface 28. In another embodiment (shown in FIG. 2), a portion of the substrate 14 is removed to define a cavity having at least two opposed posts 24, 26.

The substrate 14 may be a single material (e.g., silicon), a mixture of materials, or layers of different materials (e.g., a silicon-on-insulator (SOI) wafer (not shown)). Etching of the substrate 14 may be accomplished via anisotropic wet etching (e.g., with KOH), with directional dry etching (e.g., reactive ion etching), ion milling, and/or other like etching processes. When etching a single material, the depth of the cavity depends, at least in part, on the amount of time during which etching takes place. When etching a silicon-on-insulator wafer, the insulator of the wafer acts as an etch stop. As such, the depth of the cavity depends on the thickness of the silicon layer on the insulator. Other semiconductor-on-insulator structures may also be used. In some instances, a GaAs wafer may be used with appropriate measures taken to smooth posts 24, 26.

The nanowire(s) 12' may be grown laterally or horizontally from the substantially vertical surface of one post 24, 26 to the substantially vertical surface of another post 26, 24, and/or from substantially vertical surfaces of both of the posts 24, 26 toward each other to form nanowire 12'.

In an embodiment, the post 24, 26 vertical surfaces from which the nanowire(s) 12' are grown may be cut or polished from the substrate 14 having a (110) crystal lattice surface plane. As used herein, the (110) plane is considered to be horizontally oriented with respect to the Cartesian coordinate system. The (110) oriented posts 24, 26 further have (111) planes of the crystal lattice, at least some of which are approximately perpendicular to, and intersect with, the horizontally oriented (110) surface of the posts 24, 26. These intersecting (111) planes are referred to herein as vertically oriented (111) planes or surfaces, noting that the (111) planes are approximately vertically oriented relative to the horizontal (110) surface of the posts 24, 26.

Any suitable method may be used to grow the nanowire(s) 12'. In some embodiments, the (111) surface orientation enables growth of the nanowire(s) 12' perpendicular to the surface (i.e., in this embodiment, in a horizontal direction). In an embodiment, nanowire 12' growth is accomplished by establishing a catalyst nanoparticle (shown as 22 in FIG. 3) on the sidewall 30, 32 of the post(s) 24, 26, and exposing the catalyst nanoparticle to a precursor gas that initiates growth of the nanowire 12'. A non-limiting example of the formation of nanowires 12' is described in U.S. patent application Ser. No. 10/738,176 filed on Dec. 17, 2003 (U.S. Publication No. 2005/0133476, published on Jun. 23, 2005), which is incorporated by reference herein in its entirety.

Referring to FIGS. 1 and 2 together, the sensing device 10, 10' also includes a passivation layer 16 established on at least a portion of the nanowire 12, 12'. It is to be understood that the passivation layer 16 may be established on a portion of the surface of the nanowire 12, 12', or on all surfaces of the nanowire 12, 12'.

In an embodiment, the passivation layer 16 is established by passivating the surface of the nanowire 12, 12'. Generally, the passivation layer 16 is an intentionally well-controlled layer, such as, for example, a thermally grown $SiO_2$ layer or a monolayer of hydrogen or methyl ligands. As a non-limiting example for silicon nanowires 12, 12', passivating may be accomplished via a thermal oxidation process that affects at least a portion of the nanowire 12, 12' surface. The passivation layer 16 disclosed herein is a relatively thin layer, and in an embodiment, the thickness ranges from about 0.2 nm to about 5 nm.

Without being bound to any theory, it is believed that the addition of the passivation layer 16 decreases the area density of electronic states located at or near the surface of the nanowire 12, 12' that are capable of deleteriously affecting the electronic properties of the nanowire 12, 12'. These interface or surface states trap and store electronic charge. These trap states may uncontrollably modify the electronic properties of the underlying nanowire 12, 12', which may deleteriously or otherwise affect the sensing results. In some modes of operation, the electronic states may become charged and discharged erratically, thereby degrading the ability of the charged species being sensed to induce charge in the nanowire 12, 12' to provide the desired change in conductance of the nanowire 12, 12'. Furthermore, the number of surface states and their ability to trap charge may vary with time. As previously stated, it is believed that the passivation layer 16 reduces the occurrence of these states, and thus enhances the electronic stability of the nanowire 12, 12'.

Embodiments of the sensing device 10, 10' also include a barrier layer 18 established on the passivation layer 16. The barrier layer 18 is selected to substantially prevent one or more chemical species (that are present in an environment to which the sensing device 10, 10' is exposed) from contacting the nanowire 12, 12'. It is believed that by preventing the transmission of the chemical species, the barrier layer 18 substantially protects the nanowire 12, 12' from chemical attack, and degradation potentially resulting therefrom; and the barrier layer 18 also substantially prevents the electronic properties of the surface of the nanowire 12, 12' from changing. Furthermore, it is believed that the barrier layer 18 substantially prevents the surface of the nanowire 12, 12' from changing, for example, as a result of exposure to oxygen, water, metal ions, or other chemical species.

As such, the barrier layer 18 is selected so that it is impermeable to one or more chemical species. Non-limiting examples of materials suitable for the barrier layer 18 include SiC, $Si_3N_4$, $Al_2O_3$, diamond-like carbon, and combinations thereof. Other materials that may, under more limited conditions, be suitable for the barrier layer 18 include silicon dioxide, silicon oxynitride, non-stoichiometric silicon nitride, phosphorus-doped silicon dioxide, and combinations thereof. In an embodiment, the barrier layer 18 is established via chemical vapor deposition, atomic layer deposition, electron beam deposition, and/or combinations thereof.

The barrier layer 18 may be established to have any desirable thickness. It is to be understood, however, that the thickness of the barrier layer 18 should be thin enough such that, in the case of electric field-effect, the electric field induced by the species being sensed couples to the nanowire 12, 12'. In an embodiment, the thickness of the barrier layer 18 ranges from about 0.5 nm to about 10 nm. In another embodiment, the thickness of the barrier layer 18 ranges from about 2 nm to about 5 nm.

In some embodiments, the passivation layer 16 and the barrier layer 18 are formed of the same materials.

The sensing system 10, 10' may also include a functionalized coating 20 established on the barrier layer 18. Generally, the functionalized coating 20 promotes (or suppresses) chemical interaction with certain analytes or other substances to be tested in an environment. The functionalized coating 20 may be a composition as simple as a silicon oxide shell, or as complex as a biological receptor specifically configured to recognize a specific molecule. It is to be understood that the functionalized coating 20 selected depends, at least in part, on the type of sensing system 10, 10' that is desirable.

Non-limiting examples of suitable functionalized coatings include a self-assembled monolayer of aminopropyltrimethoxysilane, mercaptopropyltrimethoxysilane, mercaptopropyltriethoxysilane, or other mono-, di-, or tri-chlorosilane species; derivatives of biological molecules (such as DNA, polypeptides, proteins, etc.) that are capable of covalently attaching to the monolayer(s) formed on the nanowire surface; organic thin films (such as a spin coat or cast film of NAFION®, poly(methyl methacrylate) (PMMA), etc.) or derivatives thereof; or combinations thereof. It is to be understood that these functionalized coatings are illustrative, and that any suitable functionalized coating 20 may be used in the embodiments disclosed herein.

In an embodiment, the barrier layer 18 is modified prior to establishing the functionalized coating 20 thereon. This may be accomplished to promote the attachment of the functionalized coating 20 to the barrier layer 18. One example of modifying the barrier layer 18 includes exposing the barrier layer 18 to oxygen plasma, or other oxidative chemicals, such that a partial oxidized surface with terminal hydroxyl groups is formed. Such a surface facilitates the chemical reaction for bonding the functionalized coating 20 molecules to the modified barrier layer 18 surface.

Figure 3:
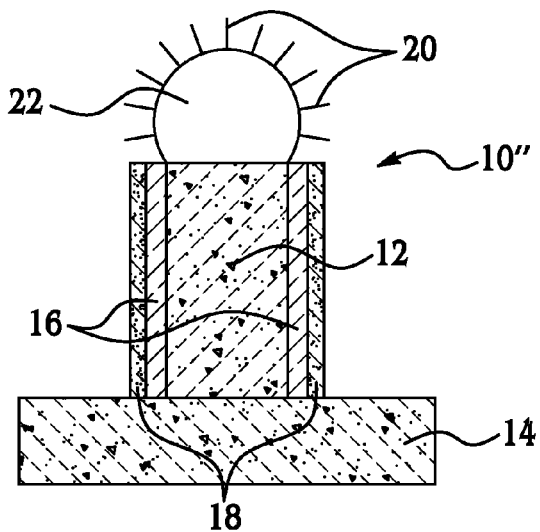
FIG. 3 is a schematic cross-sectional diagram of still another embodiment of the sensing system.

FIG. 3 depicts an alternate embodiment of the sensing system 10". In this embodiment, the catalyst nanoparticle 22 used to grow the nanowire 12, 12' remains at the tip or end of the nanowire 12, 12', and the functionalized coating 20 is established on the nanoparticle 22. It is to be understood that the functionalized coating 20 may be selectively established on the nanoparticle 22 instead of the barrier layer 18, or in addition to the barrier layer 18.

Selective deposition techniques may be used to establish the functionalized coating 20 on the nanoparticle 22 instead of on the barrier layer 18. In an embodiment, the nanoparticle 22 is selectively functionalized with ligands that bond preferentially thereto. Non-limiting examples of suitable nanoparticles 22 include gold nanoparticles, titanium nanoparticles, platinum nanoparticles, palladium nanoparticles, nickel nanoparticles, or combinations thereof. Suitable selective deposition techniques include thiol chemistry, for example, where thiol compounds self-assemble on a nanoparticle 22 surface, but not on oxide or carbon-like surfaces (e.g., barrier layer 18). Other compounds that selectively bind to some metals (e.g., gold, platinum and palladium), and may be suitable for binding to nanoparticles 22 of such metals include, but are not limited to diazonium compounds, amine derivative compounds, pyridine and derivatives thereof, or combinations thereof. It is to be understood that in embodiments in which functionalized coatings 20 are used on both the nanoparticle 22 and the barrier layer 18, the respective coatings 20 are often formed of different materials.

In an embodiment, the functionalized coating 20 is established on the catalyst nanoparticle 22 instead of along the barrier layer 18. In another embodiment, neither the passivation layer 16 nor the barrier layer 18 are established on the nanowire 12, 12', and the functionalized coating 20 is established on the catalyst nanoparticle 22 instead of along the nanowire 12, 12'. Without being bound to any theory, it is believed that such selective placement allows the target species to be sensed at a known location (e.g., at the end of the nanowire 12, 12'). Establishing the functionalized coating 20 on the catalyst nanoparticle 22 instead of the barrier layer 18 may also increase the sensitivity of the system 10" to a small amount of target species.

Still further, it is believed that if the sensing system 10" is used for mechanical resonant sensing, limiting the area from which the reflected signal is collected may increase the sensitivity of the system 10", in part by limiting signal collection to the area of maximum oscillation.

Embodiments of the system 10, 10', 10" disclosed herein may advantageously be used for chemical and/or biological sensing, with signal transduction and detection via mechanical resonant sensing, optical sensing, electrical sensing by field effect modification, and/or combinations thereof. In one embodiment, species that adhere to the nanowire surface or the functionalized coating 20 induce an electric field that modulates the electrical conductance of the nanowire 12, 12'. In another embodiment, species that adhere to the nanowire surface or the functionalized coating 20 have a mass that modifies the mechanical oscillation properties of the nanowire 12, 12' (e.g., the fundamental resonant frequency). Such resonant oscillation may be detected optically or electrically. In such embodiments, the passivation layer 16 substantially ensures a high electronic-quality nanowire surface at fabrication, and the barrier layer 18 substantially ensures that this high electronic-quality surface does not degrade upon environmental exposure. In sharp contrast, low electronic-quality surfaces or surfaces that degrade upon environmental exposure will generally produce significant instability and noise in any measured signal, including low frequency drift of the sensor response.

While several embodiments have been described in detail, it will be apparent to those skilled in the art that the disclosed embodiments may be modified. Therefore, the foregoing description is to be considered exemplary rather than limiting.

What is claimed is:

1. A sensing system, comprising:
   a nanowire;
   a passivation layer established on at least a portion of the nanowire;
   a barrier layer established on the passivation layer;
   a functionalized nanoparticle attached to an end of the nanowire; and
   a functionalized coating established on the barrier layer.

2. The sensing system as defined in claim 1 wherein the barrier layer is impervious to a chemical species present in an environment to which the sensing system is exposed.

3. The sensing system as defined in claim 1 wherein the barrier layer has a thickness ranging from about 0.5 nm to about 10 nm.

4. The sensing system as defined in claim 1 wherein the functionalized nanoparticle is selected from a gold nanoparticle having thiol compounds, diazonium compounds, amine derivative compounds, pyridine, or pyridine derivative compounds bound thereto; a titanium nanoparticle having thiol compounds bound thereto; a platinum nanoparticle having thiol compounds, diazonium compounds, amine derivative compounds, pyridine, or pyridine derivative compounds bound thereto; a palladium nanoparticle having thiol compounds, diazonium compounds, amine derivative compounds, pyridine, or pyridine derivative compounds bound thereto; and a nickel nanoparticle having thiol compounds bound thereto.

5. The sensing system as defined in claim 1 wherein the passivation layer reduces an area density of electronic interface states at a surface of the nanowire.

6. The sensing system as defined in claim 1 wherein the nanowire is selected from silicon nanowires, germanium nanowires, silicon-germanium nanowires, III-V nanowires, II-VI nanowires, and combinations thereof.

7. The sensing system as defined in claim 1 wherein the barrier layer is selected from SiC, $Si_3N_4$, $Al_2O_3$, diamond-like carbon, and combinations thereof.

8. The sensing system as defined in claim 1 wherein the passivation layer is silicon dioxide.

9. The sensing system as defined in claim 1 wherein a functionalized coating on the functionalized nanoparticle is different from the functionalized coating established on the barrier layer.

10. A method for making a sensing system, the method comprising:
    establishing a nanowire such that a first end of the nanowire is attached to a substrate and a catalyst nanoparticle is attached at a second end of the nanowire;
    forming a passivation layer on at least a portion of the nanowire;
    establishing a barrier layer on the at least a portion of the passivation layer; and
    establishing a respective functionalized coating on each of the catalyst nanoparticle and on the barrier layer.

11. The method as defined in claim 10 wherein establishing the nanowire is accomplished by:
    establishing the catalyst nanoparticle on the substrate; and
    exposing the catalyst nanoparticle to a precursor gas that initiates growth of the nanowire.

12. The method as defined in claim 11 wherein establishing the functionalized coating includes selectively functionalizing the catalyst nanoparticle with ligands that preferentially bond to the catalyst nanoparticle and selectively functionalizing the barrier layer with a material that is different from the ligands that preferentially bond to the catalyst nanoparticle.

13. The method as defined in claim 10 wherein forming the passivation layer is accomplished by a thermal oxidation process that affects the at least a portion of the nanowire.

14. The method as defined in claim 10 wherein establishing the barrier layer is accomplished by chemical vapor deposition, atomic layer deposition, electron beam evaporation, or combinations thereof.

15. The method as defined in claim 10 wherein, prior to establishing the functionalized coating, the method further comprises modifying a surface of the barrier layer to produce surface chemical groups that promote chemical bonding to compounds of the functionalized coating.

\* \* \* \* \*